US010506924B2

(12) United States Patent
Thompson et al.

(10) Patent No.: US 10,506,924 B2
(45) Date of Patent: Dec. 17, 2019

(54) HEAD AND EYE TRACKING

(71) Applicant: Auckland UniServices Limited, Auckland (NZ)

(72) Inventors: Ben Thompson, Orakei (NZ); Jason Turuwhenua, Greenlane (NZ)

(73) Assignee: Auckland UniServices Limited, Auckland (NZ)

( * ) Notice: Subject to any disclaimer, the term of this patent is extended or adjusted under 35 U.S.C. 154(b) by 136 days.

(21) Appl. No.: 14/783,588

(22) PCT Filed: Apr. 10, 2014

(86) PCT No.: PCT/NZ2014/000063
§ 371 (c)(1),
(2) Date: Oct. 9, 2015

(87) PCT Pub. No.: WO2014/168492
PCT Pub. Date: Oct. 16, 2014

(65) Prior Publication Data
US 2016/0066781 A1    Mar. 10, 2016

(30) Foreign Application Priority Data

Apr. 10, 2013  (NZ) ....................... 609259
Dec. 3, 2013   (NZ) ....................... 618558

(51) Int. Cl.
*A61B 3/113*     (2006.01)
*A61B 5/11*      (2006.01)
(Continued)

(52) U.S. Cl.
CPC .............. *A61B 3/113* (2013.01); *A61B 3/145* (2013.01); *A61B 5/0077* (2013.01);
(Continued)

(58) Field of Classification Search
CPC ............................ A61B 5/0084; A61B 5/0059
See application file for complete search history.

(56) References Cited

U.S. PATENT DOCUMENTS 5,704,369 A *  1/1998  Scinto .................... A61B 3/112
                                                600/558
7,380,938 B2   6/2008  Chmielewski, Jr. et al.
(Continued)

FOREIGN PATENT DOCUMENTS

EP    2261772 A1    12/2010
JP    H10146319 A    6/1998
(Continued)

OTHER PUBLICATIONS

Lee, Inbum, et al., "Robust measurement of ocular torsion using iterative Lucas-Kanade", Computer Methods and Programs in Biomedicine 85 (2007) 238-246, (Dec. 11, 2006), 238-246.
(Continued)

*Primary Examiner* — Hien N Nguyen
(74) *Attorney, Agent, or Firm* — Schwegman Lundberg & Woessner, P.A.

(57) ABSTRACT

Embodiments of the invention relate to a method of extracting eye velocity information from a video footage having a plurality of frames, comprising detecting at least part of an eye in at least two frames of the video footage, applying an optical flow algorithm to the at least two frames of the video footage to extract pixel velocity information, and determining a statistical measure from the pixel velocity information within the detected at least part of the eye. Other embodiments of the invention relate to a method of extracting head image trajectory information from a video footage having a plurality of frames, comprising detecting at least part of a facial region of the head image in at least two frames of the video footage, determining a measure of the movement of
(Continued)

the at least part of a facial region between the at least two frames, and determining a transformation map from the measure of the movement.

20 Claims, 11 Drawing Sheets

(51) Int. Cl.
| | | |
|---|---|---|
| *A61B 3/14* | (2006.01) | |
| *G06T 7/00* | (2017.01) | |
| *A61B 5/00* | (2006.01) | |
| *G06T 7/269* | (2017.01) | |

(52) U.S. Cl.
CPC ........... *A61B 5/1114* (2013.01); *A61B 5/1128* (2013.01); *G06T 7/0012* (2013.01); *G06T 7/269* (2017.01); *G06T 2207/20076* (2013.01); *G06T 2207/30041* (2013.01); *G06T 2207/30201* (2013.01); *G06T 2207/30241* (2013.01)

(56) References Cited

U.S. PATENT DOCUMENTS

| | | |
|---|---|---|
| 2005/0073136 A1 | 4/2005 | Larsson et al. |
| 2006/0274079 A1* | 12/2006 | Oyaizu ................... G06T 13/80 345/582 |
| 2010/0329513 A1* | 12/2010 | Klefenz ................. G01C 21/00 382/104 |
| 2012/0068858 A1* | 3/2012 | Fredkin ............ G08G 1/096741 340/902 |
| 2014/0172555 A1* | 6/2014 | Argue ................. G06Q 30/0633 705/14.49 |

FOREIGN PATENT DOCUMENTS

| | | |
|---|---|---|
| JP | 2004504684 A | 2/2004 |
| JP | 2005013626 A | 1/2005 |
| WO | WO-2003/017203 | 2/2003 |
| WO | WO-2008/129356 | 10/2008 |
| WO | WO-2014/168492 | 10/2014 |

OTHER PUBLICATIONS

Ong, James K.Y., et al., "Measuring torsional eye movements by tracking stable iris features", Journal of Neuroscience Methods 192 (2010) 261-267, (Aug. 2, 2010), 261-267.

Sanders, Brandon C. S., "Opportunistically Learning Relevant Objects in Real Environments", Thesis Proposal for the Degree Doctor of Philosophy, Department of Computer Science, University of Rochester, Rochester, New York, (2002), 59 pgs.

Wendong, Zhou, et al., "An Eye Feature Extraction Based on Harris Algorithm", GCSE 2011, Dec. 28-30, 2011, Dubai,UAE, Procedia Engineering, (2011), 1-6.

Yu, Tzu-Ying, "Assessing visual function and motion processing in 2-year-old children", Presentation at the Southern Regional Congress of Optometry, Victoria, (2012), 4 pgs.

"International Application No. PCT/NZ2014/000063, International Search Report and Written Opinion dated Jul. 9, 2014", (Jul. 9, 2014), 19 pgs.

Bourel, Fabrice, et al., "Robust Facial Feature Tracking", Proceedings of the British Machine Vision Conference, BMVC 2000, BMVA Press, Sep. 2000, (Sep. 2000), 10 pgs.

Garbutt, S., et al., "Abnormalities of optokinetic nystagmus in progressive supranuclear palsy", J Neurol Neurosurg Psychiatry 2004;75:1386-1394, (2004), 1386-1394.

Pieters, R. S., "Active Vision: Directing Visual Attention", Master's Thesis, DCT 2008.145, Technische Universiteit Eindhoven, Department Mechanical Engineering, Eindhoven, Nov. 2008, (Nov. 2008), 95 pgs.

Viola, Paul, et al., "Robust Real-Time Face Detection", International Journal of Computer Vision 57(2), 137-154, 2004, (2004), 137-154.

Tunhua, Wu, et al., "Real-time Non-Intrusive Eye Tracking for Human-Computer Interaction", Computer Science and Education (ICCSE), 2010 5th International Conference on Computer Science & Education, IEEE, Aug. 24-27, 2010, p. 1092-1096, (Aug. 24, 2010), 1092-1096.

"European Application No. 14 783 494.9, Communication under Rule 71(3) EPC dated Dec. 20, 2018", (Dec. 20, 2018), 7 pgs.

* cited by examiner

Frame number

HEAD AND EYE TRACKING

PRIORITY CLAIM TO RELATED APPLICATIONS

This application is a U.S. national stage application filed under 35 U.S.C. § 371 from International Application Serial No. PCT/NZ2014/000063, which was filed 10 Apr. 2014, and published as WO 2014/168492 on 16 Oct. 2014, and which claims priority to New Zealand Application No. 609259, filed 10 Apr. 2013, and to New Zealand Application No. 618558, filed 3 Dec. 2013, which applications and publication are incorporated by reference as if reproduced herein and made a part hereof in their entirety, and the benefit of priority of each of which is claimed herein.

FIELD OF THE INVENTION

The invention generally relates to systems and methods for processing video information useful for the determination of optokinetic nystagmus and head movement.

BACKGROUND

Accurate evaluation of visual function in young children in particular is challenging. There are few methods available and none are particularly suitable for use by health care providers who do not have extensive training in pediatric ophthalmology, optometry and/or visual electrophysiology.

Optokinetic nystagmus (OKN) is the phenomena of involuntary eye movement triggered by a continuously moving pattern or stimulus, and can be used to evaluate visual function. OKN is the repetition of an eye moving to smoothly pursue a target in a visual stimulus followed by a resetting event (saccade) where the eye fixes on a new target of the stimulus. FIG. 1(b) shows a graph of eye displacement over time showing a saw tooth OKN profile that is characteristic of OKN eye movement.

The presence or absence of OKN is an objective indication of visual performance and can also be useful for assessing neurological disorders. Early detection of a vision problem in a person's life is also known to significantly improve the outcome of proceeding treatment.

An OKN visual stimulus consists of an arrangement of lines or dots having modifiable properties including contrast, frequency or coherence. Manipulating these parameters allows measurement of the threshold at which OKN is no longer present. This threshold is a measure of visual performance.

One method of eliciting OKN is with use of a spinning hand-held drum that has a visual stimulus. A clinician watches eye movement to make a decision regarding the presence or absence of OKN.

Another method of detecting OKN is known as electro-oculography. Electrodes placed around the eye measure changes in electrical potential as the eye (a strong dipole) moves in response to a visual stimulus. The signals produced by the electrodes are analysed to determine the presence or absence of OKN.

Another method of detecting OKN is with the use of video-oculography techniques. The position of an eye is tracked by reviewing live or recorded video. Video-oculography is appealing because it is a non-invasive and can be implemented using low cost and basic video hardware. U.S. Pat. No. 7,380,938 describes a video-oculography technique where video footage of an eye is recorded, the vertical and horizontal movement of an eye isolated and displacement of the eye in the vertical and horizontal directions is measured. The displacement measurement can be analysed to determine the presence or absence of OKN patterns.

One disadvantage of video-oculography techniques is that they require a fixed positional relationship between the camera and eyes in order to eliminate performance errors introduced by head movement. To prevent head movement, the subject is often required to place their head in a fixed chin-rest or wear head mounted equipment such as cameras and lighting equipment to improve the video recording. Young children and infants do not tolerate head fixing or head-mounted gear which precludes them from an objective assessment of their visual function using video-oculography techniques.

Objects of the present invention relate to ways of assess optokinetic nystagmus which overcomes or at least ameliorates some of the abovementioned disadvantages or which at least provides the public with a useful choice.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

SUMMARY OF THE INVENTION

In one broad aspect the invention consists in a method of extracting eye velocity information from a video footage having a plurality of frames, comprising detecting at least part of an eye in at least two frames of the video footage, applying an optical flow algorithm to the at least two frames of the video footage to extract pixel velocity information, and determining a statistical measure from the pixel velocity information within the detected at least part of the eye.

In another broad aspect the invention consists in a eye tracking system comprising a camera arranged to capture footage of an eye, a controller configured to receive the footage of the eye and perform the steps of detecting at least part of an eye in at least two frames of the footage, applying an optical flow algorithm to the footage to thereby determine pixel velocity information between at least two frames of the footage, and determining a statistical measure from the pixel velocity information within the detected at least part of the eye.

In another broad aspect the invention consists in a controller device programmed to perform the steps of detecting at least part of an eye in at least two frames of the footage, applying an optical flow algorithm to the footage to thereby determine pixel velocity information between at least two frames of the footage, and determining a statistical measure of the pixel velocity information within the detected at least part of the eye.

Some embodiments further comprise one or more of the steps of (in any order): determining the velocity magnitude and direction of at least part of an eye from the velocity information, determining any velocity maxima and minima from the velocity information, comparing any maxima or minima to a lower velocity threshold and discarding any maxima or minima below the threshold, comparing any maxima or minima to an upper velocity threshold and discarding any maxima or minima above the threshold, comparing the inter-frame distance between adjacent maxima or minima to a frame threshold and discarding any maxima or minima below the frame threshold, determining any sole maxima or sole minima in the velocity information and discarding sole maxima or sole minima, averaging the maxima or minima velocity magnitudes, and/or normalising the maxima or minima velocity magnitudes.

In some embodiments the statistical measure of the pixel velocity information is an average pixel velocity.

In some embodiments the at least part of the eye is a region of contrast discontinuity of the eye.

In some embodiments the at least part of the eye is a limbus portion of the eye.

Some embodiments further comprise generating a list of pixel velocity averages for each consecutive frame in the video footage.

Some embodiments further comprise comparing the determined velocity information to healthy velocity information to make a determination of the health of the eye and/or visual pathway.

Some embodiments further comprising comparing the determined velocity information to healthy velocity information to make a determination of the presence and/or strength of OKN.

In some embodiments the limbus portion of the eye is determined by an edge detection algorithm.

In some embodiments edge detection is performed by application of a Prewitt operator.

In some embodiments the optical flow algorithm is a Lucas-Kanade optical flow algorithm.

In some embodiments the optical flow algorithm is applied to determine pixel velocity information between consecutive frames of a length of video footage corresponding to several reset events.

Some embodiments further comprise a visual stimulus arranged in front of the eye, the stimulus operable to elicit optokinetic nystagmus.

Some embodiments further comprise comparing the average velocity information to known optokinetic nystagmus velocity information to make a determination of the health of an eye in response to the stimulus.

In some embodiments the video footage is obtained from a subject watching a stimulus.

In some embodiments the stimulus is a screen.

In some embodiments the camera and screen are contained within an enclosure.

In some embodiments the camera, screen and controller are integrated within an enclosure.

In some embodiments the enclosure is any one or more of a smart phone, tablet or portable computation device.

In some embodiments detecting at least part of an eye does not include detection of a feature of the eye.

In another broad aspect the invention consists in a method of improving the attention of a subject for eye tracking comprising operating at least one display to show a video of an video functional to gain the attention of a viewer, operating at least one display to show an OKN stimulus video, and recording an eye watching the OKN stimulus video with a camera.

In some embodiments the video functional to gain the attention of a viewer is an animated video.

In some embodiments the method further comprises the method of extracting eye velocity information from the recording of the eye according to claim 1.

In some embodiments the statistical measure is applied to determine information relating to one or more of a person's behaviour, a person's response to advertising, security purposes, or consumer attention.

Some embodiments further comprise extracting head image trajectory information from the video footage by a method comprising detecting at least part of a facial region of the head in at least two frames of the video footage, determining a measure of the movement of the at least part of a facial region between the at least two frames, and determining a transformation map from the measure of the movement.

Some embodiments further comprise determining the inverse of the transformation map, applying inverse of the transformation to each frame in the video footage such the facial region within the frame is held substantially constant.

Some embodiments further comprise detecting the facial region from within a frame of the video footage using the Viola-Jones algorithm.

Some embodiments further comprise identifying one or more particular portions of the facial region within the frame using a Harris corner detection algorithm.

Some embodiments further comprise determining the measure of the movement of the facial region or one or more particular portions of a facial region between consecutive video frames using a Kanade Lucas Tomasi (KLT) point tracker.

In some embodiments the measure of the movement comprises one or more of rotation, scale and/or translation movement.

In some embodiments the transformation map is created from the movement information.

Some embodiments further comprise applying an inverse similarity transformation to offset each frame in the video footage such that the facial region within the frame is held substantially constant with respect to each frame.

Some embodiments further comprise applying an inverse similarity transformation to crop each frame in the video footage to generate a new frame such that the facial region within the frame is held substantially constant with respect to each frame.

In some embodiments the head trajectory information is used to improve the eye velocity information.

In some embodiments head trajectory information is offset against the eye tracking information to substantially remove eye velocity information caused by head movement.

In another broad aspect the invention consists in a method of processing video footage having a plurality of frames to determine the presence of OKN, the method comprising: extracting head trajectory information by a method comprising detecting at least part of a facial region of the head image in at least two frames of the video footage, determining a measure of the movement of the at least part of a facial region between the at least two frames, and determining a transformation map from the measure of the movement, and extracting eye velocity information by a method comprising detecting at least part of an eye in at least two frames of the video footage, applying an optical flow algorithm to the at least two frames of the video footage to extract pixel velocity information, and determining a statistical measure from the pixel velocity information within the detected at least part of the eye.

In some embodiments the head trajectory information is offset against the eye tracking information to substantially remove eye velocity information caused by head movement.

In another broad aspect the invention consists in a method of extracting head image trajectory information from a video footage having a plurality of frames, comprising: detecting at least part of a facial region of the head image in at least two frames of the video footage, determining a measure of the movement of the at least part of a facial region between the at least two frames, and determining a transformation map from the measure of the movement.

In another aspect the invention consists in a method of extracting head image trajectory information from a video footage having a plurality of frames, comprising: detecting at least part of a facial region of the head image in at least two frames of the video footage, determining a measure of the movement of the at least part of a facial region between the at least two frames, and determining a transformation map from the measure of the movement.

In another aspect the invention consists in a head tracking system for extracting head image trajectory information comprising: a camera arranged to capture footage of a head and a controller configured to receive the footage of the head and perform the steps of: detecting at least part of a facial region of the head in at least two frames of the video footage, determining a measure of the movement of the at least part of a facial region between the at least two frames, and determining a transformation map from the measure of the movement.

In another aspect the invention consists in a controller device configured to perform the steps of detecting at least part of a facial region of the head in at least two frames of the video footage, determining a measure of the movement of the at least part of a facial region between the at least two frames, and determining a transformation map from the measure of the movement.

In some embodiments the method or steps further comprise: determining the inverse of the transformation map, applying inverse of the transformation to each frame in the video footage such the facial region within the frame is held substantially constant.

Some embodiments further comprise detecting the facial region from within a frame of the video footage using the Viola-Jones algorithm.

Some embodiments further comprise identifying one or more particular portions of the facial region within the frame using a Harris corner detection algorithm.

Some embodiments further comprise determining the measure of the movement of the facial region or one or more particular portions of a facial region between consecutive video frames using a Kanade Lucas Tomasi (KLT) point tracker.

In some embodiments the measure of the movement comprises one or more of rotation, scale and/or translation movement.

In some embodiments the transformation map is created from the movement information.

Some embodiments further comprise applying an inverse similarity transformation to offset each frame in the video footage such that the facial region within the frame is held substantially constant with respect to each frame.

Some embodiments further comprise applying an inverse similarity transformation to crop each frame in the video footage to generate a new frame such that the facial region within the frame is held substantially constant with respect to each frame.

In some embodiments the system or method is to be applied to infants, young children or impaired persons.

In some embodiments the system or method is to be applied to children under 10 years old.

In some embodiments the system or method is to be applied to children under 8 years old.

In some embodiments the system or method is to be applied to children under 6 years old.

In some embodiments the system or method is to be applied to children under 4 years old.

In some embodiments the system or method is to be applied to children under 2 years old.

In some embodiments the system or method is to be applied to children up to 2 years old.

In some embodiments the system or method is to be applied to children up to 3 years old.

In some embodiments the system or method is to be applied to children up to 4 years old.

The following embodiments may relate to any of the above aspects. Other aspects of the invention may become apparent from the following description which is given by way of example only and with reference to the accompanying drawings.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement or claim, all need to be present but other features can also be present. Related terms such as "comprise" and "comprised" are to be interpreted in the same manner.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

The invention will now be described by way of example only and with reference to the drawings in which:

FIG. 1(a) illustrates the region of an eye typically monitored for change in displacement. FIG. 1(b) shows a graph of eye displacement over time exhibiting a saw tooth profile characteristic of healthy eye movement. FIG. 1(c) shows a graph of eye velocity derived from the eye displacement signal.

FIG. 2(a) is an example image of an eye received from a camera. FIG. 2(b) shows an example of pixel velocity vectors provided by an optical flow algorithm. FIG. 2(c) is an example of a graph of the regional velocity average of the optical flow velocity vectors.

FIG. 4(a) shows an example input edge similar in size ($\sigma=5$) to that observed in. FIG. 4(b) shows calculated response curves (for three examples velocities (v=1; 3; 5 pixels/frame respectively) using saccade velocity values indicative of what would be encountered in practice.

FIG. 5 (inset left) shows an example of a low coherence stimulus. FIG. 5 (inset right) shows an example of a full coherence stimulus.

DETAILED DESCRIPTION

Eye Tracking

Figure 1:
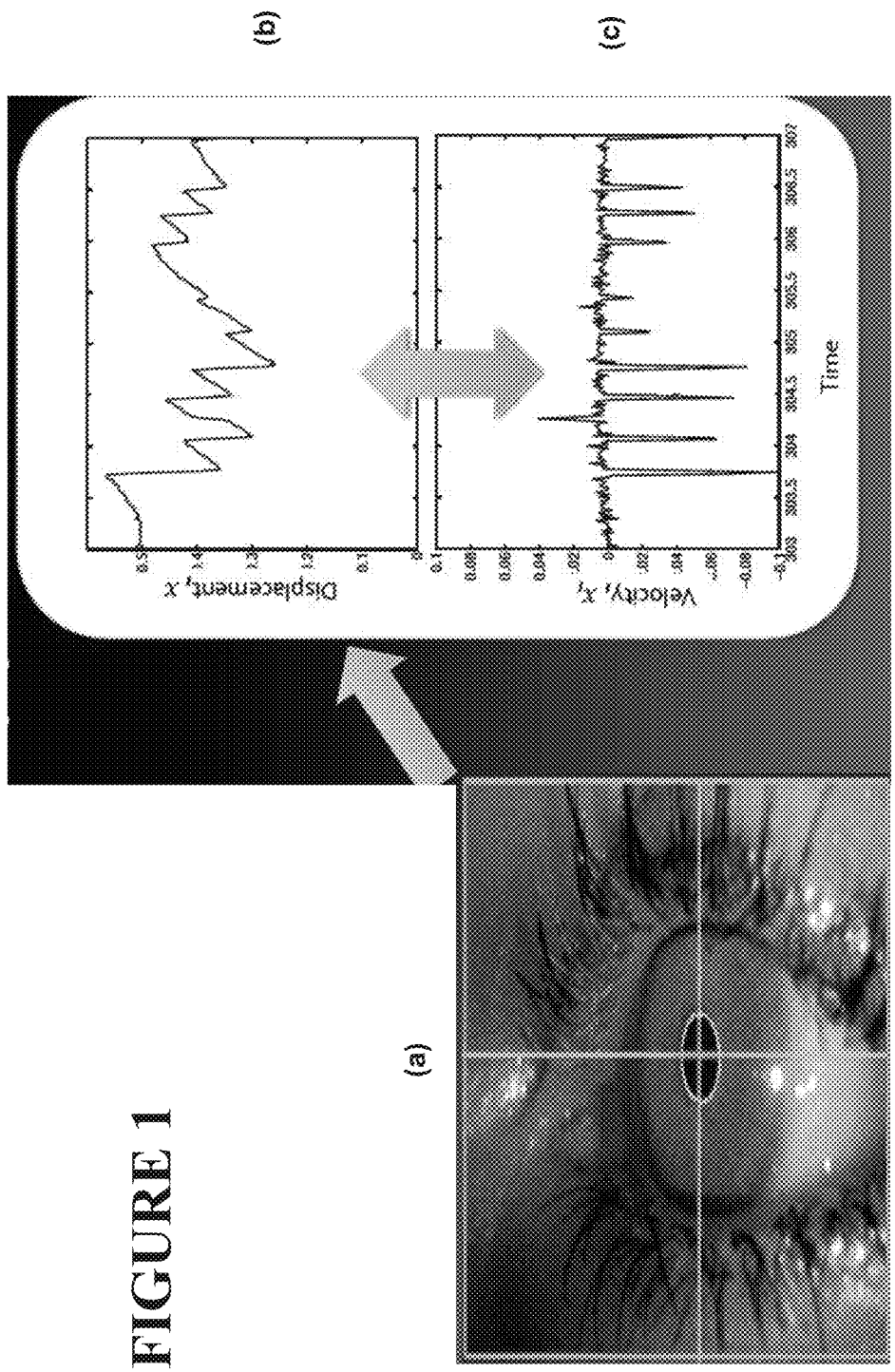
FIG. 1 shows a picture of an eye.

Video-oculography techniques of the prior art require a location in an image for processing by an edge detection algorithm primarily acting on the contrast transitions in the image. The location must therefore be a high contrast feature of the eye such as the pupil, limbus edge or eyelids. Movement of these features can be tracked from frame to frame to determine a displacement signal. The footage recorded by a standard RGB camera will typically produce a poor contrast between features of the eye, particularly for dark irises. FIG. 1(a) illustrates poor contrast in a frame in a video recording. FIG. 1(a) also shows how the image can be further contaminated by corneal reactions, eye-lashes and eye-lids. To improve the contrast of these features in a video recording, and therefore the performance of the edge detection algorithm, infra-red light is used to illuminate the eye. Head mounts or chin rests may be used to stabilize the eyes relative to the recording equipment. However, young subjects are adverse to head mounted equipment and having their heads fixed in place.

One particular embodiment is a video-oculography system and method that allows detection of OKN from video footage. The video footage is used to make an estimate of the velocity, rather than the displacement, of an eye as a subject watches a visual stimulus. In particular, the invention includes determining a velocity estimate of pixels inside the coarse determination of a limbal region of an eye by application of an image processing algorithm known as optical flow. In preferred embodiments, a Lucas-Kanade optical flow algorithm is used. A significant advantage of this approach is that precise edge detection is not required which improves the robustness of the system and method when working with poor image contrast and other issues that give rise to image distortion. The system and method are also insensitive to stationary obstructions such as eyelids or eyelashes that often confound displacement based approaches of the prior art. Further, detection of particular aspects or features of the eye, for example specks, lines or a clear edge that exist within the eye, is not required. Further, measurement of torsional movement is not required.

The velocity estimate provided by the optical flow algorithm is an average of the pixel velocities in the coarsely determined limbal region. Heuristic analysis may be applied to the determined velocity estimate to determine the presence and direction of OKN. The velocity estimate information, such as shown in FIG. 1(c), may also be manually compared to healthy eye velocity information, and in particular the velocity threshold at which OKN is no longer present, to make a comparative judgement of the health of the eye and/or the visual pathway. The velocity estimation may also be used to track the direction of a person's gaze. The direction of the gaze may be used to judge behavioural characteristics of a person including information such as what visual stimulus gains their attention.

In one embodiment the system is applied to pre-recorded video footage. While in another embodiment the system is applied in real time to the video signal from a camera. Various embodiments are combined with a visual stimulus presentation system designed to elicit an OKN response. A portable or handheld device having both a camera and a computational power, such as a smart phone, tablet or laptop device may be useable. However, those skilled in the art will recognise that devices separately capable of displaying an appropriate stimulus and recording video footage may be used.

The velocity information obtained from the optical flow algorithm is used to detect whether or not the stimulus has elicited OKN in a subject's eye. The stimulus parameters at the threshold where OKN is no longer detected provides an indication of visual performance. A clinician may review the velocity information determined from the eye movement. Alternatively, a statistical analysis process may be applied to the velocity information to determine the presence or absence of OKN.

According to some embodiments, the statistical process is calculating a regional average velocity of the optical flow field determined from a region of the eye. In some embodiments, the limbal region of the eye is used where the limbal region is coarsely determined from an edge detection process. In other embodiments, other regions or a combination of regions of the eye are used which provide at least a contrast discontinuity, such as the iris. The contrast discontinuity is used to track a region of the eye from which velocity information is to be analysed.

Lucas-Kanade feature tracking may also be used to track head movement. Eye movement may be quantified and also head movement may be quantified. Determination of head movement may negate the requirement for head mounted video equipment.

Figure 5:
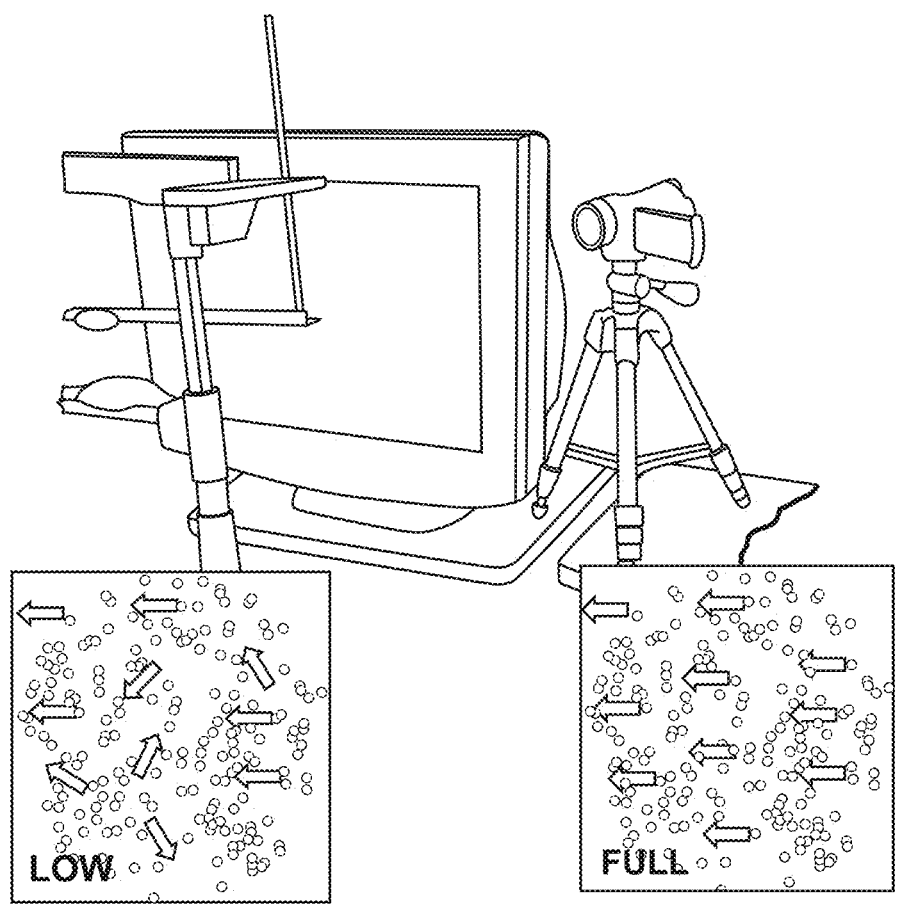
FIG. 5 shows an arrangement of one example of components including a camera located proximate a display to present a clear line of sight to view the eyes.

One example of a visual stimulus used to elicit OKN is a visual display with 250 moving white dots, on a 16" cathode ray tube (CRT) as shown in FIG. 5. Those skilled in the art will recognise the display may be any screen of adequate size and resolution relative to that of the stimulus video to be displayed. For example, a CRT screen, LCD or handheld display may be used. In some embodiments, the dots are around 0:5° in size and presented in a 8:3° circular window for around 8 seconds. In some embodiments, the dots move at around 8.3°/second. In some embodiments, the proportion of dots moving in concert versus the total population of dots is adjustable. Full dot coherence has 100% of the dots moving in the same direction, such as shown in FIG. 5, inset right, while low dot coherence has between 30-38% of all dots moving in concert, whilst the rest moved randomly such as shown in FIG. 5, inset left. In some embodiments, the coherence of the dots is also adjustable.

In one example, a CRT display is placed at a distance of approximately 60 cm from a subject's eyes. Video footage is collected using a SONY digital high definition camera (HDR-CX7EK, Sony Corporation, Tokyo, Japan) delivering video footage of RGB images (1920 by 1080 pixels) at 25 frames per second. A camera is located proximate the display to present a clear line of sight to view the eyes. This arrangement (without the subject) is shown generally in FIG. 5.

In another example, in particular to improve the attention of young test subjects, the visual stimulus video is interspersed with a video segment that appeals to children, such as a cartoon. A cartoon or other kind of animated video is displayed for a period of time adequate to gain the attention of a young subject before the visual stimulus video is displayed for a period of time adequate to acquire OKN data. The cartoon can be displayed when attention wanes or alternatively when the OKN video has finished. The cartoon may be switched to and from the display automatically by a control device or manually by an operator. In another example, the cartoon may be displayed on a first screen and the OKN stimulus video on a second screen. The first screen is switched on to gain the attention of a subject, then the second screen is switched on and the first screen off so that the subject views the OKN stimulus.

Figure 11:
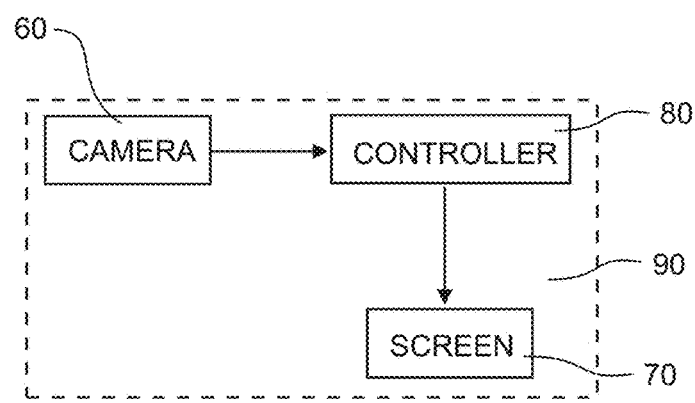
FIG. 11 shows an overview of the components of the system including the camera, a screen and a computational device.

In some embodiments, the video footage is input to system such as a computational device capable of processing video data. One example of such a system is a PC running MATLAB software. The computational device is equipped with hardware and software for receiving video footage and performing manipulation and analysis of that footage. Alternatively the computational device may be a standalone system such as a microprocessor or microcontroller. FIG. 11 shows an overview of the components of the system including the camera 60 for recording the eye footage, a screen 70 for displaying the stimulus and a computational device 80. Each of these components may be contained within an enclosure 90 such as a smart phone or tablet as previously described.

The method of determining OKN according to various embodiments is conducted according to the following steps. A video sequence containing footage of eye is recorded while the eye watches a stimulus. In some embodiments, the video is colour and high definition, for example, 1920 by 1080 pixels, but may also be black and white and/or a lower definition. In some embodiments, the video footage is reduced to grey scale to reduce computation complexity. An optical flow image processing algorithm is applied to the video footage to determine pixel velocity information from sequential frames. The velocity information is determined from a limited region of the eye and that region is the limbus and/or limbal edge portion of the eye. The region is a coarse estimate of the limbal region of the eye determined by an edge detection algorithm. The image processing algorithm outputs optical flow information represented by pixel velocity information in determined the limbus region of the eye over two consecutive frames in the video footage. The pixel velocity information, including the speed and direction, can be directly assessed to determine the presence and direction of OKN.

Figure 3:
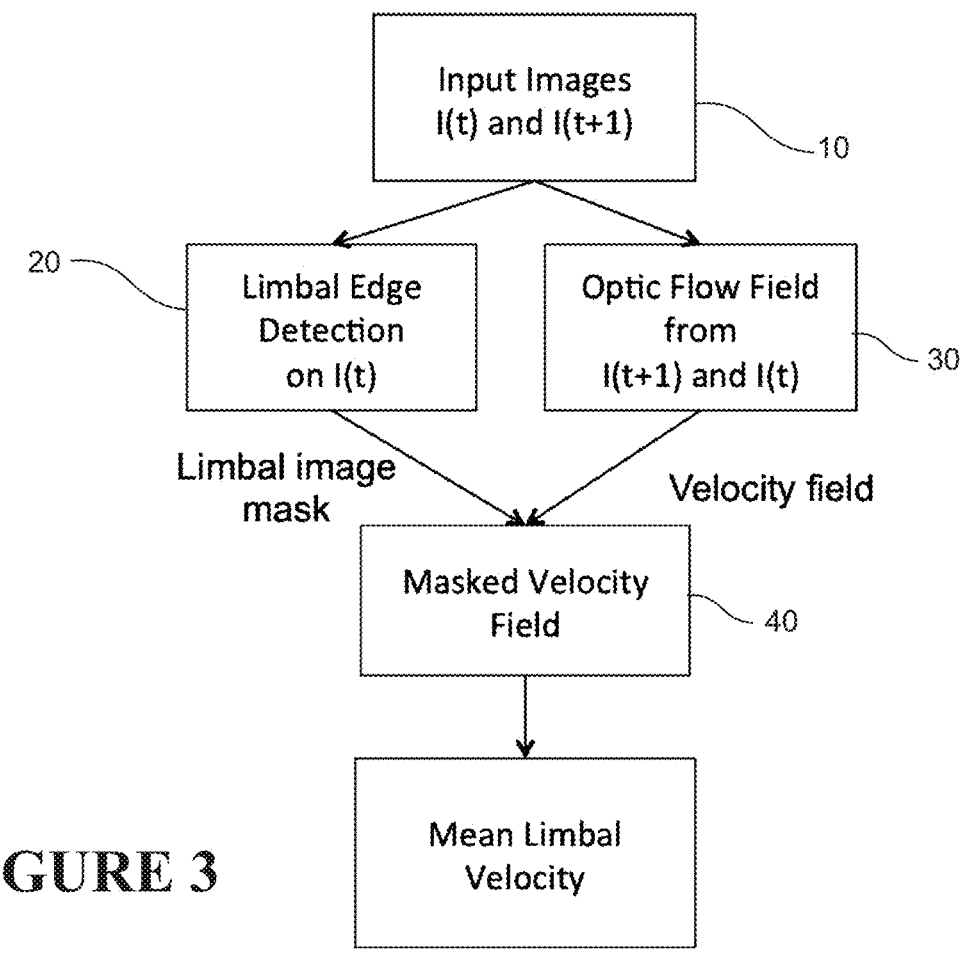
FIG. 3 shows an outline of the preferred process steps of the invention.

One example of the steps of the process is shown in FIG. 3 where the transformation of two consecutive image frames into an estimate of pixel velocity is shown. In a first step 10, consecutive video frames I(t) and I(t+1) are taken from high definition colour video footage and reduced to gray scale. In a second step 20, a coarse determination of the limbal region of the eye is determined by an edge detection process applied to the video footage to determine an edge map. The edge map represents a determination of the location of the limbus portion of the eye and therefore the area of the video footage from which optical flow information is to be determined. The edge map does not need to be precisely determined for the optical flow information to be useful. The process is robust to variation in the limbal edge maps obtained throughout frames in the video footage. The edge detection is ideally performed by application of a Prewitt operator with hysteresis thresholding. However, those skilled in the art will recognise other edge detection strategies or operators could be used to determine the limbal region. Connected regions under a certain weight and regions connected to the image border are removed. In a third step 30, which may be processed concurrently or before the second step 20, an optical flow estimation process determines pixel velocity information from spatial and temporal changes in pixel intensity. As shown in FIG. 1(c), a limbal region should exhibit a velocity spike during a rapid resetting event of an eye (saccade) and smooth or constant velocity changes during other periods when a stimulus is being observed.

Figure 2:
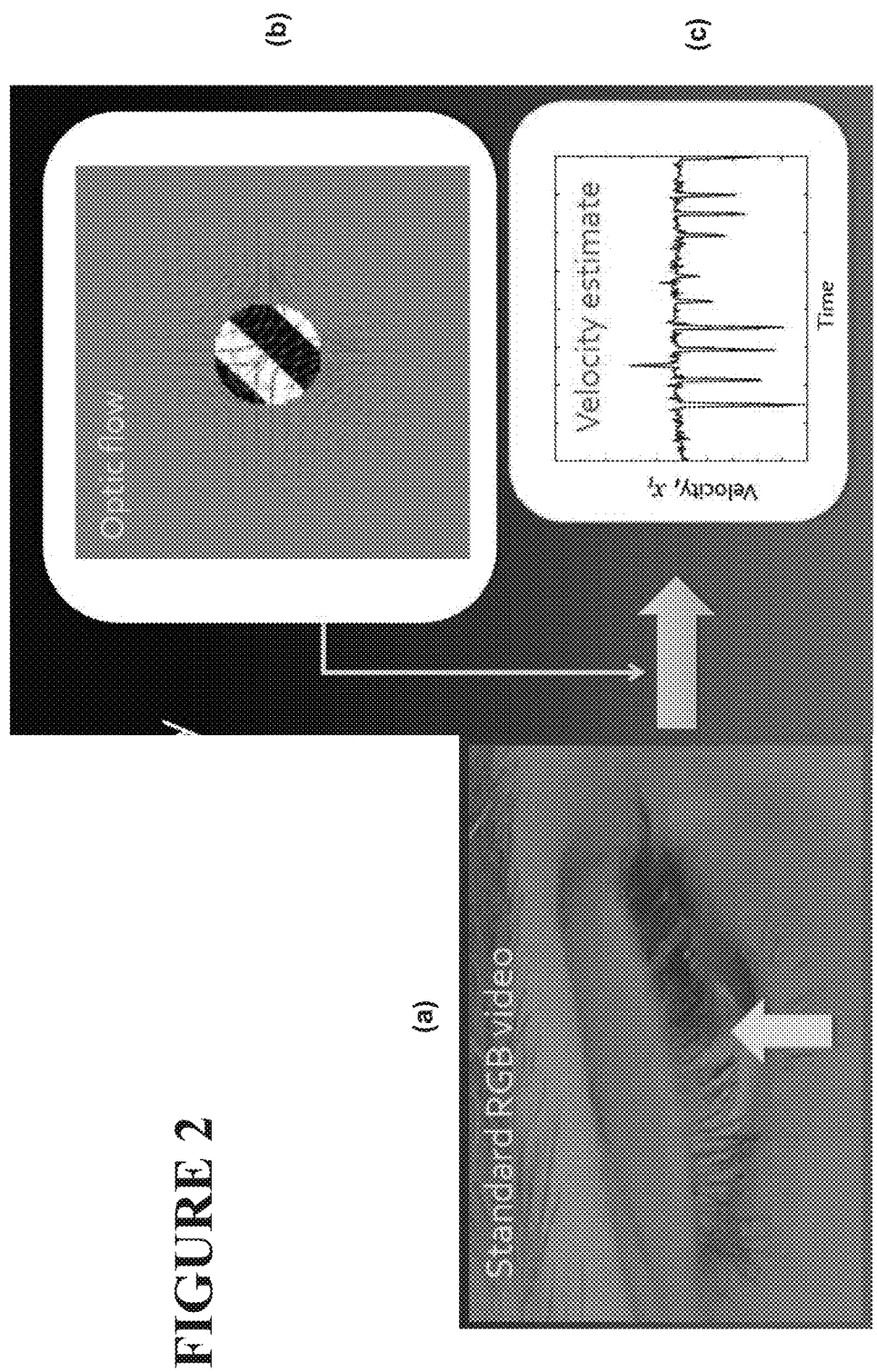
FIG. 2 shows an example where consecutive image frames are transformed into an estimate of pixel velocity.

FIG. 2 shows the optical flow process in greater detail. FIG. 2(a) shows an image or single frame of a piece of video footage showing an eye. FIG. 2(b) shows a number of vectors indicating the magnitude and direction of pixel travel between consecutive frames. FIG. 2(c) is a graph of the average velocity of the pixel vectors of FIG. 2(b) for a number of consecutive frames.

In the fourth step 40 of FIG. 3, the limbal region information provided by the edge detection process 20 is combined with the pixel velocity information provided by the optical flow process 30 to produce a masked velocity field. The masked velocity field represents velocity information only within the detected limbal region. In a fifth step 50, the velocity information from the masked velocity field is averaged to produce a velocity value for a given pair of consecutive frames in the video footage. The process of FIG. 3 is performed on as many consecutive frames in the video footage as desired such that a graph of velocity is provided as a function of time. The graph can then be analysed to determine OKN information.

Figure 10:
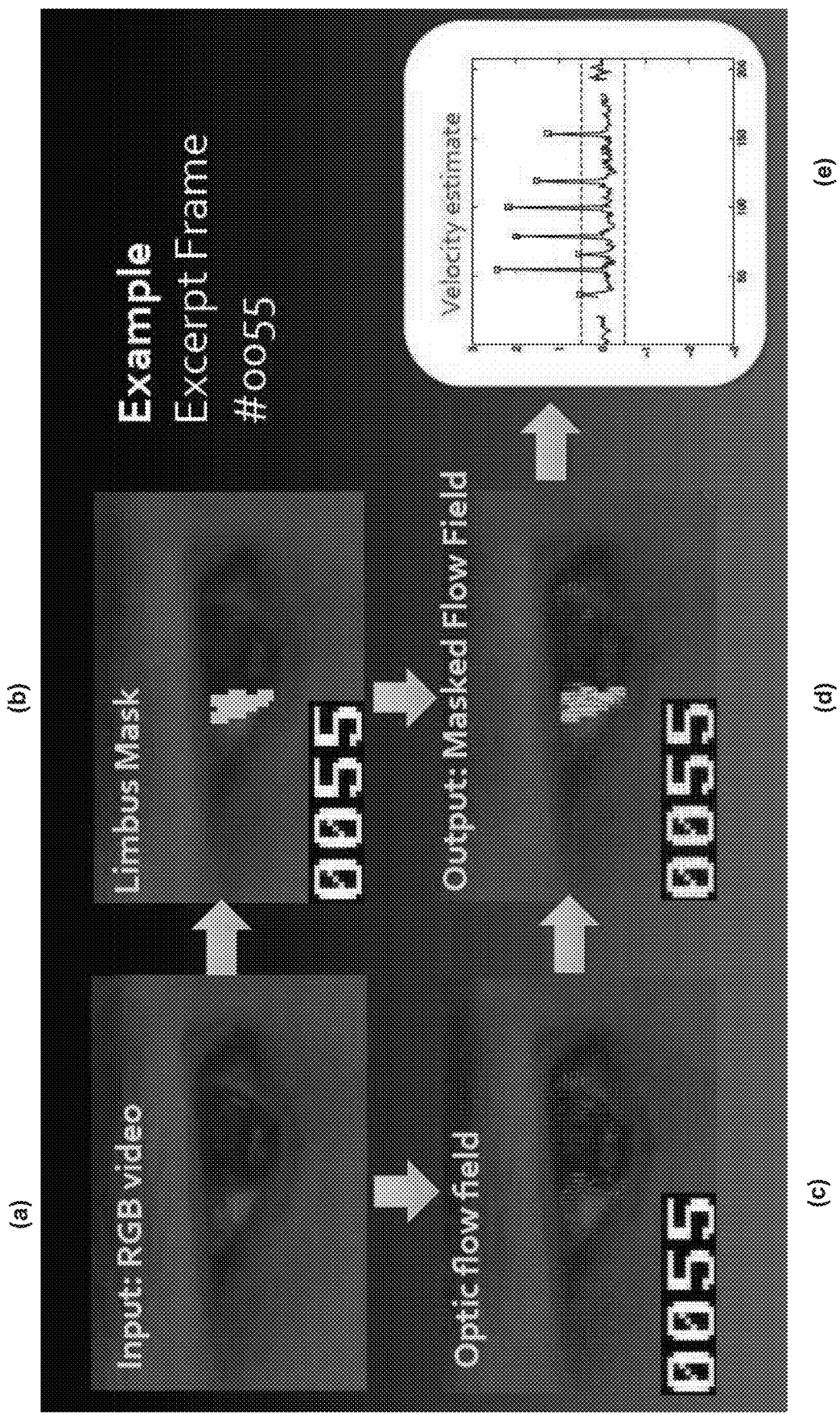
FIG. 10 shows the process of FIG. 3 applied to a single frame, frame 0055, in a piece of video footage.

FIG. 10 shows the process of FIG. 3 applied to a single frame, frame 0055, in a piece of video footage. FIG. 10(a) shows an image of an eye input to the process. FIG. 8(b) shows the limbal region identified by the edge detection process. FIG. 10(c) shows the optical flow estimation of pixel velocity. FIG. 10(d) shows the detected limbal region overlaid with the detected velocity information. FIG. 10(e) shows the resultant average velocity information of the optical flow velocity information within the detected limbal region.

The optical flow estimation equation is provided below as equation 1.

$$I_t = -\nabla I(x,y,t) \cdot V \tag{1}$$

And in simple 1D form as equation 2.

$$V = \frac{-I_t}{I_x} \tag{2}$$

Equation 3 shows a sigmoidal 1D edge (representing the limbus) with a rising intensity edge travelling to the right over time.

$$I = \frac{1}{1 + e^{-(x-vt)/\sigma_l}} \quad (3)$$

Confirmation of V=v is provided by the derivatives of equation 3 being substituted into equation 2. Errors in estimating the pixel velocity will arise from noise, digitization, and the assumptions of small temporal or spatial displacements used in deriving equation 1. However, the expected response can be observed from equation 2.

Figure 4:
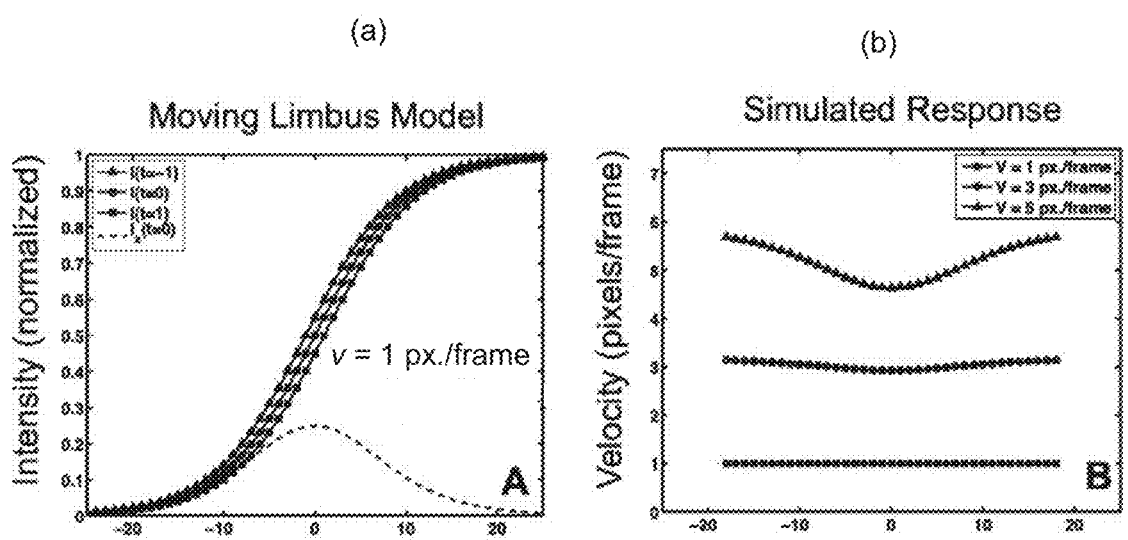
FIG. 4 shows graphs of simulated limbal edge and detector response.

FIG. 4(a) shows an example input edge similar in size ($\sigma$=5) to that observed in practice at three consecutive frames indexed by t=-1, 0, 1 (in this case, the edge has a velocity of v=1 pixels/frame). Also shown is the scaled spatial derivative of intensity $I_x$ (scaled by 5 for illustrative purposes) taken at t=0.

FIG. 4(b) shows calculated response curves (over a [-20; +20] pixel interval) for three examples velocities (v=1; 3; 5 pixels/frame respectively) using saccade velocity values indicative of what would be encountered in practice. The response curves show the velocity estimate as a function of position. The mean ($\overline{V}$) and standard deviation ($\sigma_{\overline{V}}$) of the response curve provides descriptors of the response for a given frame t. The response to the v=1 edge is both unitary and indicates accurate velocity estimation ($\overline{V}$=1.0), ($\sigma_{\overline{V}}$=0.0).

Measurable responses to edges are expected at saccadic velocities. The above analysis also suggests more accurate velocity estimations at lower velocities, with increased deviation from true velocity (toward saturation), as true velocity increases. The velocity information obtained is sufficient to detect a saccadic movement and therefore make a determination of the presence or absence of OKN.

A modification to the one dimensional description to facilitate detection of saccadic movements in two dimensional video is possible. In some embodiments, the optical flow algorithm is a Lucas-Kanade method. However, those skilled in the art will recognise that other optical flow measurement methods may also be used where appropriate. An assumption of the Lucas-Kanade optical flow algorithm is that V is constant over a small region (with pixels indexed i=1, . . . , n) centred on the pixel p. The least squares estimate of velocity at p is shown in equation 4.

$$V(p) = (A^T W A)^{-1} A^T W b \quad (4)$$

Where, $$A = \begin{bmatrix} I_x(1) & I_y(1) \\ I_x(2) & I_y(2) \\ \vdots & \vdots \\ I_x(n) & I_y(n) \end{bmatrix}, V(p) = \begin{bmatrix} V_x(p) \\ V_y(p) \end{bmatrix}, b = \begin{bmatrix} I_t(1) \\ I_t(2) \\ \vdots \\ I_t(n) \end{bmatrix}$$

and W is the diagonal n×n matrix shown in equation 5.

$$W = \text{diag}(w(1), w(2), \ldots, w(n)) \quad (5)$$

W is the weight contribution of pixels within the local region around p as desired. A Gaussian window may be used. The limbal velocity is the mean of all V(p) over the limbus region and as represented by equation 6, $$\overline{V} = \begin{cases} \frac{\sum_p q(p) V(p)}{\sum_p q(p)} & \text{if } \sum_p q(p) > 0 \\ \text{undefined} & \text{if } \sum_p q(p) = 0 \end{cases} \quad (6)$$

where p varies over pixels in an image containing the eye. In some embodiments, the following weighting factor q(p) is used as shown in equation 7, $$q(p) = \begin{cases} 1 & \text{if } p \in \Omega \\ 0 & \text{if } p \notin \Omega \end{cases} \quad (7)$$

where $\Omega$ are the set of pixel indices within the image classified as limbus.

A video-oculography technique for determining eye velocity information has been described. The technique is substantially robust against the error induced by head movements seen in normal adult fixations, eye blinks, reflections and other error inducing factors. Further, the technique may be combined with head stabilisation for use with young children or subjects who would not tolerate head mounted equipment. The technique is therefore a video-oculography technique readily applicable to infants or young children who would otherwise be unable to be assessed. The technique may be implemented with standard 'off the shelf' video equipment thereby avoiding the need for expensive supporting hardware. The velocity information graph resulting from the above described technique can be analysed directly by a trained clinical professional and/or further processed by an OKN detection process that will now be described.

Figure 9:
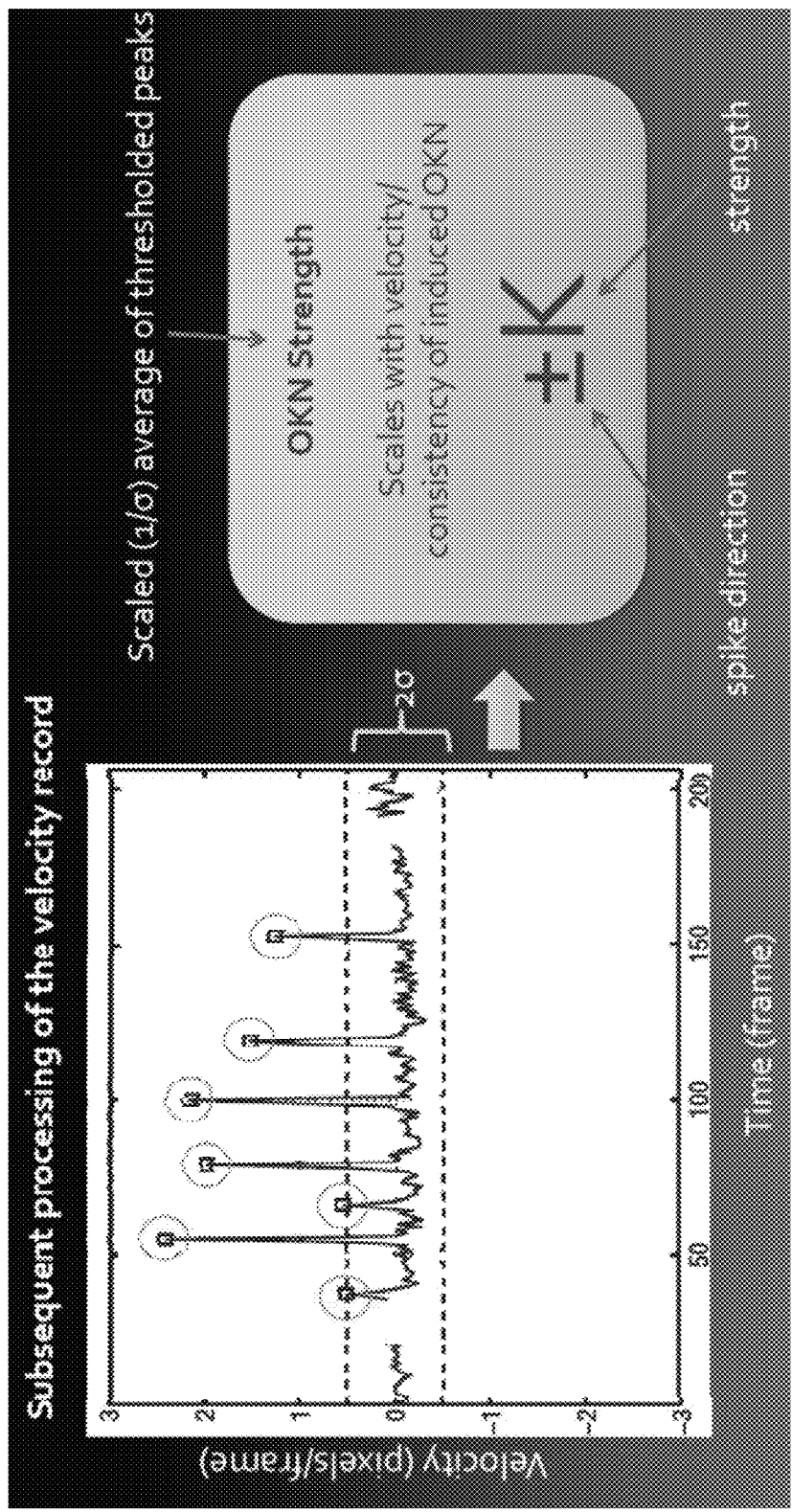
FIG. 9 shows a graph of peaks in the velocity information.

OKN strength can be determined by the following. Peaks not indicative of OKN are rejected, for example, by comparing them to a threshold and discarding those peaks below the threshold. An average of the heights of the surviving peaks is determined and scaled by an appropriate normalization value $1/\sigma_{\overline{V}}$. A low value will result if peaks are weak or equally distributed between positive and negative. Conversely, if peaks are consistently positive or negative, the measure will scale with the average height, and the sign will correlate with the direction of the reset event. FIG. 9 shows a graph of peaks in the velocity information.

A more detailed explanation of the process step for detection of OKN from the obtained velocity information according to various embodiments is provided below:

1. Detect all maxima and minima within the given interval of $V_x(t)$ signal and label them Q(j), where j=1 . . . M. A maxima (or minima) is defined as a point with neighbouring points less (or more) than a test point by an absolute threshold of $\sigma_{peak}$ pixels per frame.
2. Compare a threshold to these peaks and eliminate all peaks |Q(j)|<$\sigma_{\overline{V}}$ smaller than an empirically determined velocity threshold. Reset M to the number of remaining peaks.
3. Reject minima (or maxima) that are above (or below) the axis if they do not indicate a reversal in the direction of the eye. A valid velocity peak should in principle, cross the axis defined by zero velocity: the slow-phase and quick-phase occurs in opposite directions (and hence are of opposite sign). This rule also assists with identifying "jagged edges" or noise that may occur on the face of a valid velocity peak. Again, reset M to the number of remaining peaks.

4. Reject peaks that are less than a given number of frames apart ($\sigma_t$). A saccadic movement should follow a period of smooth pursuit. A very short latency period is unusual for OKN. In some embodiments, a threshold of 4 frames corresponding to 133 to 160 ms (for camera frame rates of 30 Hz and 25 Hz) is used. In some embodiments the expected slow phase interval for a stimulus moving at 10 deg/s is estimated to be greater than 250 ms. Again, reset M to the number of remaining peaks.

5. In some embodiments a solitary maxima or minima or minima is rejected (i.e., those with no other peaks of the same sign in the data). An isolated peak is often not enough evidence to support a determination of OKN. Again, reset M to the number of remaining peaks.

6. Determine the normalised average peak velocity $\overline{K}$. If there are remaining peaks then take $\overline{K}$ as the mean of the velocities after normalisation by the velocity threshold $\sigma_T$. In some embodiments the threshold is set to 0.5 pixies per frame. If there are no remaining peaks, set the $\overline{K}$ to zero, as shown by equation 8:

$$\overline{K} = \begin{cases} 1/(M\sigma_V)\sum_{j=1}^{M} Q(j) & M > 0 \\ 0 & M = 0 \end{cases} \quad (8)$$

The sign of $\overline{K}$ determines the direction of the OKN reset event. For positive $\overline{K}$ the reset event will be rightward, whilst for negative $\overline{K}$ it will be leftward. The magnitude will indicate the consistency of OKN within the data. An absolute value of $\overline{K}$ less than 1 indicates the absence of consistent saccadic movements indicative of OKN. A value of $\overline{K}$ of greater than or equal to 1 indicates the presence of consistent saccadic movements, and hence OKN.

The following description of experimental work further illustrates the invention.

Experimental Data Part 1

To test the performance of the detection process, video footage of healthy eyes was recorded for six participants of average age twenty five. Footage obtained was prepared for further processing by manually cropping the video around each eye. The video recording was cut to a temporal length corresponding to the temporal length of the stimulus. In this case, the stimulus was eight seconds. A total of one hundred and fifteen in-focus trials were obtained from participants where seventy there were obtained for a full coherence stimulus and forty two for a low coherence stimulus. The stimulus coherence was expected to alter the OKN response of the eye.

The velocity estimator and OKN detector were applied to each resulting video record. The sign of the resulting OKN strength measure was used as an indicator of OKN direction. The optical flow algorithm used was a version written by Dollar (2012) named the Lucas-Kanade optical flow solver.

The first seventeen trials were recorded using a pure stimulus pattern with 100% coherence. These trials were used to calibrate the parameters for later use. Trial accuracy was 100% for our calibration set of seventeen trials (9 correct left detections, 8 correct right detections) after appropriate adjustment of all algorithm parameters.

Figure 6:
FIG. 6 shows a sequence of video frames obtained from the calibration trials that illustrate aspects of the detection process.
Figure 7:
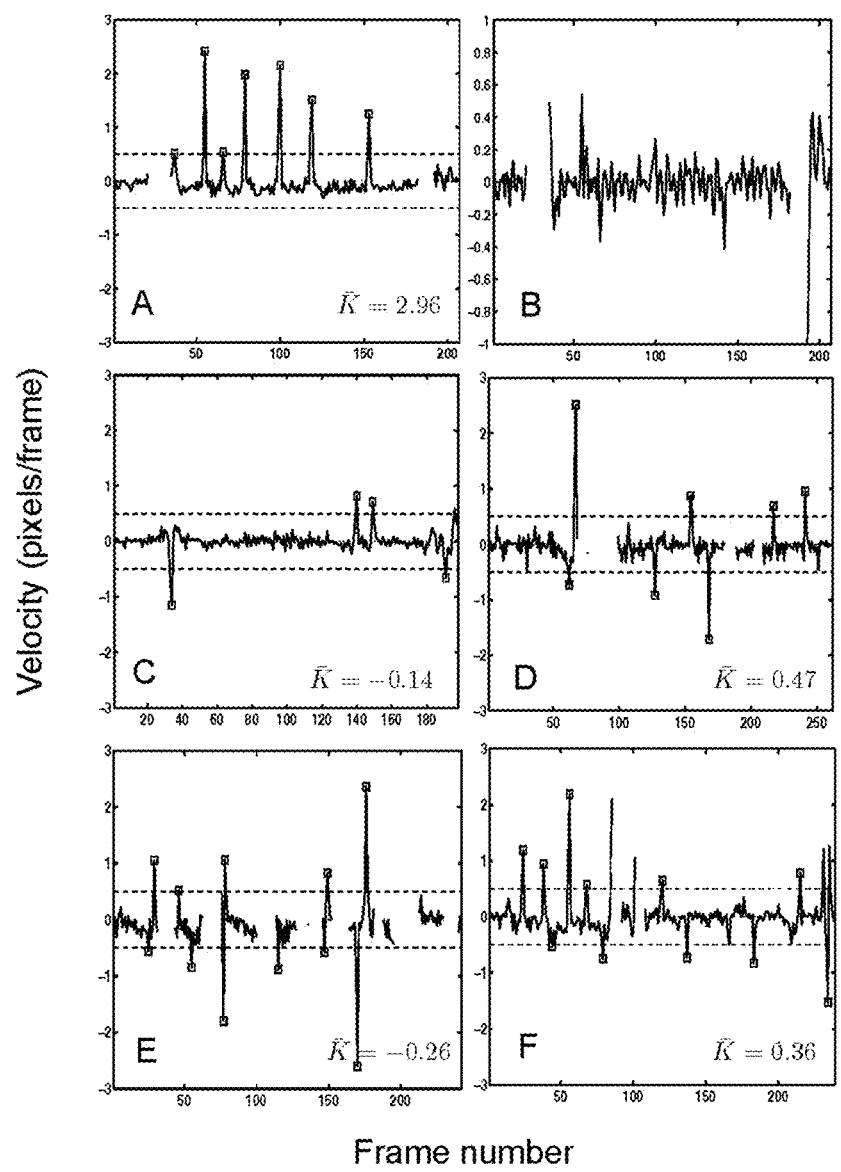
FIGS. 7(a)-(f) show pixel velocity information and OKN consistency values $\overline{K}$.

FIG. 6 shows a sequence of video frames obtained from the calibration trials that illustrate aspects of the detection process. The estimated limbal region is overlaid over grey-scale images of the eye. Frame 10 shows a resting eye, whilst frames 54-56 show the occurrence of an OKN reset event. Frame 26 demonstrates the loss of the limbus edge during an eye blink. These observations are further confirmed by inspection of the horizontal and vertical velocity traces for this sequence as shown in FIGS. 7(a) and 7(b). The frame numbers that appear in the bottom left corner of the stills in FIG. 6, correspond directly to the horizontal axis of FIGS. 7(a) and 7(b). The peaks accepted as OKN data are shown boxed.

An empirically set velocity threshold of 0.5 pixels per frame is also shown as a dotted line. The performance of the detector over all 115 trials was 93% with 52 correct left detections, 53 correct right detections and 10 errors. The performance of the detector for the full coherence group was 96% with 38 correct left detections, 32 correct right detections and 3 errors. The performance of the low coherence group was 88% with 14 correct left detections, 21 correct right detections and 7 errors.

Figure 8:
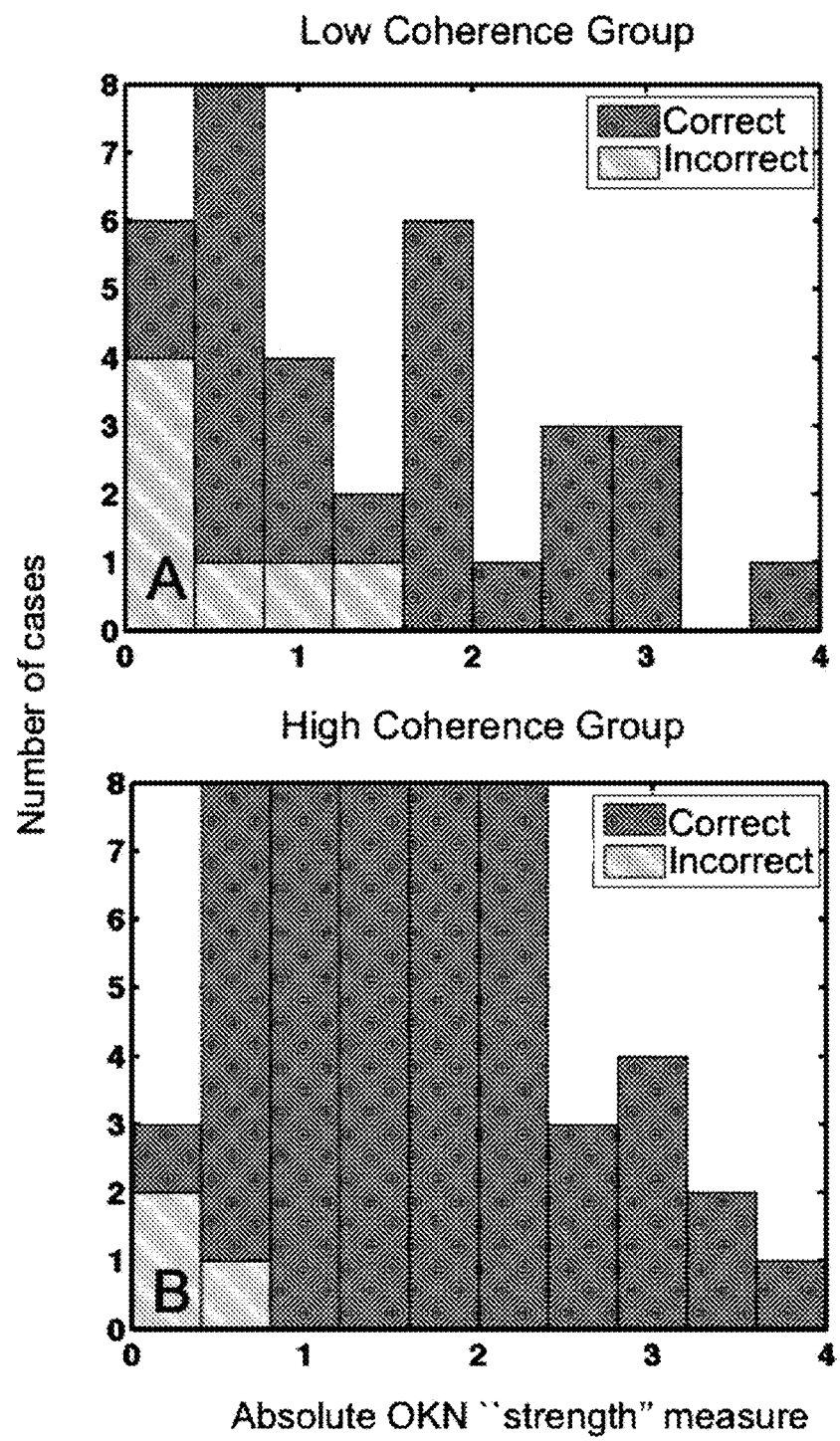
FIG. 8 shows a summary of the distribution of OKN consistency values $\overline{K}$.

The actual distribution of OKN consistency values $\overline{K}$ is summarized by FIG. 8. The histogram illustrates the distribution of $\overline{K}$ across the two groups which indicate the distributions of correct and incorrect distributions. It is probable that incorrect detections are correlated with low OKN values. There are two likely possibilities for this observation. That the OKN spikes occur infrequently and with low magnitude, and/or the OKN spikes are distributed about zero velocity resulting in a low average.

The three incorrect detections are shown in FIGS. 7(c), (d) and (e), whilst the final panel, (f), shows a correct detection with a marginal OKN assessment (i.e., close to the mean of the incorrect cases). Bi-directional peaks appear to cancel each other out resulting in a low OKN consistency measure. To confirm this observation, the videos for these cases were reviewed by an expert observer and it was deemed that the recordings indeed contained sequences of OKN in which direction changed. The peaks were therefore not attributable to spurious errors inherent to the method.

Experimental Data Part 2

The aims this experiment were to assess whether the OKN detection algorithm could correctly classify OKN eye movements as going left or right and to compare the performance of the OKN detector to that of an experienced human observer (TY). For this experiment we used a random dot kinematogram (RDK) with variable motion coherence to elicit OKN. This stimulus was chosen as the perception of global motion within such stimuli is thought to rely on dorsal areas of the extrastriate visual cortex that may be particularly vulnerable to abnormal development. An RDK can elicit reliable slow and fast-phase optokinetic eye movements to measure motion coherence thresholds in young children who cannot yet provide behavioural responses to psychophysical tasks.

The RDK consisted of 250 moving white dots (0.5 deg diameter, 8 deg/sec speed), presented at 100% contrast on a 16" CRT display. The dots were presented in 8.3° circular window for 8 sec and had a limited lifetime whereby each dot had a 25% chance of dying on any given frame and being replotted in a new, random location within the stimulus. Dots that reached the edge of the stimulus aperture were wrapped around. The coherence level of the stimulus, i.e., the proportion of dots moving in the same direction versus the total population of dots could be adjusted to vary the strength of coherent motion present in the stimulus. We tested full coherence (i.e., 100% of the dots moved in the same direction) and low coherence (between 12-15% of all dots moved in concert, whilst the rest moved randomly). The direction of coherent motion was randomized across trials. The low coherence level was chosen to be suprathreshold for our observers (i.e. the global motion direction was still clearly visible) while still allowing us to test the algorithm on eye movements elicited by degraded motion signals. The 1600 CRT display was viewed from 50 cm. Video footage was collected using a SONY digital high definition camera (HDR-CX7EK, Sony Corporation, Tokyo, Japan), that delivered video consisting of RGB images (1920×1080 pixels) at 25 frames per second. The camera was placed to the side of the CRT, and centred on the closest eye.

Six participants with a mean age of 25 years and normal vision viewed the RDK stimuli binocularly with their head restrained by a chin rest. A fixation point was presented in the centre of the CRT screen before and after each RDK presentation trial. Participants were instructed to fixate on the point in between trials and stare at the centre of the screen during trials. The fixation point was not presented during a trial. Footage obtained from the trials was prepared for further processing by manually cropping the video around each eye within every trial. The video for each trial was cropped temporally to include only frames recorded when the participant was viewing the motion stimulus. A total of 115 trials (of 8 sec length) were obtained from the participants (73 at full coherence and 42 at low coherence). The participants were able to perceive the direction of the signal dots in each trial as indicated by behavioural responses provided during testing.

The velocity estimator and OKN detector were applied offline to each resulting video record. The detector estimated $\overline{K}$. The absolute value of $\overline{K}$ was thresholded to indicate the presence ($\overline{K} \geq 1$) or absence ($\overline{K} \leq 1$) of OKN. The sign of the measure indicated the direction. The first 17 trials were recorded using the 100% coherence stimuli and were used to calibrate the parameters for the method. Software was written using MATLAB, and we used an implementation of the Lucas-Kanade optical flow solver. The video footage was also viewed by an experienced human observer (TY) who made a 2-alternative forced choice decision as to whether the OKN response was consistent with a left or right moving RDK. The observer was not aware of the results generated by the detection algorithm when viewing the videos. We achieved 100% accuracy for our calibration set of 17 trials (9 correct left detections, 8 correct right detections), after appropriate adjustment of all algorithm parameters.

The performance of the detector over all 115 trials was 93%, (54 correct left detections, 53 correct right detections, 8 errors) compared to 98% (53 correct left detections, 60 correct right detections, 2 errors) for the human observer. The performance of the detector for the full coherence trials was 96% (38 correct left detections, 32 correct right detections, 3 errors) compared to 100% (38 correct left detections, 35 correct right 14 detections) for the human observer.

For the low coherence trials the detector performed at 88% correct (16 correct left detections, 21 correct right detections, 5 errors) compared to 95% correct for the human observer (15 correct left detections, 25 correct right detections, 2 errors), also a non-significant difference (Chi-Square=1.40, p=0.24). For the full coherence trials 3/3 (100%) incorrectly classified trials had K values less than 1 compared to $18/70$ (26%) for the correctly classified trials (Chi-Square=7.7, p<0:005). Similarly for the low coherence trials 5/5 (100%) incorrectly classified trials had K values less than 1 compared to $17/37$ (46%) for the correctly identified trials (Chi-Square=5.0, p=0.02). An inspection of the velocity traces for the incorrectly classified trials indicated that low values were due to velocity peaks being relatively equally distributed around zero. These bi-directional peaks appeared to cancel each other out resulting in a low OKN consistency measure.

To confirm this observation, the video footage of the 8 trials incorrectly classified by the detector was reviewed for a second time by an experienced human observer (TY). It was confirmed that bi-directional velocity spikes resulted from actual eye movements visible within the video footage and was not caused by spurious errors of the method. It was also found that the recordings indeed contained sequences of OKN in which direction changed.

Experimental Data Part 3

This experiment had three aims: to assess whether the OKN consistency measure was affected by stimulus velocity, to assess whether the OKN detector would correctly reject trials during which participants passively viewed a stationary stimulus, and to assess whether the detection technique could be applied to footage obtained using a standard webcam. A high contrast square-wave grating stimulus was used for experiment as this type of stimulus is used routinely to induce OKN in clinical studies.

An IBM P275 cathode ray screen (2000 screen, a resolution of 1600×1200 and 60 Hz refresh rate) screen was viewed from 1.9 m on which were presented a 100% contrast square wave grating with a fundamental spatial frequency of 3.8 cycles/deg (equivalent to 0.9 Log MAR). Three presentation velocities (0 deg/s, 5 deg/s and 10 deg/s) were used, and the grating always moved right to left. Video footage of the OKN eye responses was obtained using an HD Pro 920 Logitech webcam (set at a 30 Hz frame-rate) positioned 10 cm from the participants eye. The stimuli were presented whilst simultaneously recording the video feed from the webcam.

A group of five observers with mean age=23 and normal vision viewed the stimuli patterns binocularly and were instructed to stare at the centre of the drifting stimulus pattern during the stimulus presentation period. Observer's heads were restrained using a chin rest. Each observer completed one trial of each stimulus velocity (0, 5 and 10 deg/s). Eye movements were recorded for a minimum of 8 seconds and the recordings were processed using the optic flow methods described above.

The limbus detection parameters were modified to account for the larger image of the eye that resulted from positioning the camera closer to the eye. In experiment 1, groupings of pixels with a weight below 20 were discarded. In this experiment, the threshold was increased to 300 pixels to account for the increased size of the recorded limbus. It is also noted that an additional heuristic rule was introduced in this experiment. If two subsequent peaks were detected (in the same direction), but the time interval between subsequent saccadic peaks was greater than a 4 second threshold, then it was assumed that the interval between the peaks was not consistent with being due to the slow phase of OKN. In the absence of additional neighbouring peaks (of the same sign) these two peaks would be discarded.

For the stationary stimuli, velocity traces either did not pass through the algorithm to allow estimation of $\overline{K}$ (3/5 traces) or $\overline{K}$ did not exceed threshold (2/5 traces, $|\overline{K}| \leq 0:6$ pixels/frame). The direction of all moving stimuli was classified correctly by the detector and the $|\overline{K}|$ values for the 5 deg/s trials did not differ significantly from those for the 10 deg/s trials (5 deg/s mean $|\overline{K}|=2.38$, SD=0.15; 10 deg/s mean $|\overline{K}|=2.85$, SD=0.62; t=1.45, p=0.22).

The OKN detector was sensitive to the presence or absence of OKN when provided with web-cam footage of participants viewing square wave grating stimuli. In the case where valid OKN was detected, the $|\overline{K}|$ values produced by the OKN detector did not change when the stimulus velocity was doubled suggesting that this measure for detecting OKN is relatively robust to stimulus velocity.

Testing therefore indicates that the embodiments herein described can detect OKN elicited by RDKs and square wave gratings and has an accuracy that is comparable to that of an experienced human observer. Objectively evaluation of visual function in young children is therefore possible by using involuntary, reflexive eye movement of OKN. In particular, children of 2 or approximately 2 years old have been found to especially benefit from the information the invention can provide.

The above described embodiments have use in the fields of advertising and security. For example, the direction of a person's gaze may be tracked to determine information relevant to consumer interest or behaviours.

Head Tracking

As previously discussed, children do not tolerate chinrests or head mounted eye-tracking equipment. Further, head movements within video footage with the above described OKN detection process can inadvertently be interpreted as eye movement and detrimentally affect the accuracy of eye movement measurements. However, such equipment has previously been thought to be the only method of retrieving stable video footage of eye movement from persons unable to remain still.

Further embodiments of the invention relate to the determination of head movement within video footage, and optionally compensating for that determined head movement. Accurate determination of head movement allows chinrests or head mounted equipment to be disregarded and the above described OKN detection process to be optimised.

In some applications, head movement information is quantified and used in conjunction with the above-described OKN analysis system to mitigate errors introduced by excessive head movement that are inadvertently determined to be eye movement. In other applications, head movement information is used independently from the above described OKN analysis system.

According to a particular embodiment, head movement information is obtained from video footage by a process, ideally undertaken by a computational system that comprises:
  detecting at least part of the same facial region in at least two frames of the video footage,
  determining a measure of the movement of the at least part of the same facial region between the at least two frames, and
  determining transformation information corresponding to the determined measure of the movement.

Robust facial features comprise areas of distinctive colour or shading contrast that are easily identified by a camera. Lighting adjustments are optionally applied to the subject and/or the video footage is processed to improve distinction of facial features. In some embodiments one or more robust facial features within a facial region are determined so that their movement can be tracked.

The facial features are identified in at least two frames of video footage and tracked by determining movement information relating to those facial features between the at least two frames. The movement information is quantified by a metric such as the number of pixels in the frame. The movement information relates to planar movement and may optionally further relate to rotation or scale movement.

The transformation information relates to movement of the head within the video frame. The transformation information is used to stabilise the head movement within the frame by moving or cropping the frame to compensate for the movement of the head.

In some embodiments, the movement information is used to produce a transformation map that contains data relating to one or more of rotation, scale and translation movement of the facial features, and therefore the head, within the video footage. A similarity transformation map determined for each frame of the video footage, with respect to a first or prior frame, provides rotation, scale and translation movement information for the head image within that frame.

In some embodiments, video footage is processed by a computer or control device (controller) capable of undertaking computational instructions. The controller calculates and applies an inverse of the transformation map to offset each frame in the video footage to generate a new frame position. The outcome is that the head portion of the footage within the frame remains relatively still and is therefore stabilised to one location whilst the frame moves by the transformed amount. In some embodiments, the controller calculates and applies an inverse of the transformation map to is actively crop and centre each frame about the region of interest, such as the facial region or eye region, to produce new video footage with that portion centred and stabilised within each frame.

The stabilised head position is useful for improving the performance of, for example, the above mentioned OKN detection process as head movement no longer substantially affects eye movement data obtained from the processed footage. In some embodiments the portion of the frame containing the eyes is cropped such that stabilised footage of the eyes is obtained for further OKN analysis, such as use with the above described automated OKN detection method. The information gathered by this process is similar to or the same as the information gathered when a person has had their head fixed in place by a chin rest or if head mounted equipment was to be used. Yet this process does not require the burden of such equipment.

In some embodiments a non-reflective similarity transformation map is created using the POSIT algorithm which estimates translation and rotation information of a 3D object from a 2D video frame. At least four 3D model points (world-space coordinates) and corresponding 2D image points, focal length and principal point of camera are needed for accurate estimation. The 3D model point coordinates, for example, the marker corners, are fixed and the corresponding 2D image points identified. The camera properties are estimated using equations (9)-(11) as shown below.

$$f_x = f_y = \frac{\frac{w}{2}}{\tan\left(\frac{120}{2} \times \frac{\pi}{180}\right)} \quad (9)$$

$$c_x = \frac{w}{2} \quad (10)$$

$$c_y = \frac{h}{2} \quad (11)$$

In these equations the terms $f_x$ and $f_y$ are the focal lengths in x and y directions respectively (assumed to be equal) and are expressed in pixel units. The image dimensions are given by (w, h), the principal point of the camera by ($c_x$, $c_y$). Rodrigues' rotation formula is used to retrieve rotations for X, Y, Z directions respectively. A POSIT error assessment is performed by reprojecting 3D model points to the 2D image plane by the transformation presented in equation (12).

$$s\begin{bmatrix}x\\y\\1\end{bmatrix}=\begin{bmatrix}f_x & 0 & c_x\\0 & f_y & c_y\\0 & 0 & 1\end{bmatrix}\begin{bmatrix}r_{11} & r_{12} & r_{13} & T_x\\r_{21} & r_{22} & r_{23} & T_y\\r_{31} & r_{32} & r_{33} & T_z\end{bmatrix}\begin{bmatrix}X\\Y\\Z\\1\end{bmatrix} \quad (12)$$

In equation (12), s is the pixel size, x and y are 2D image points, X, Y and Z are 3D model coordinates, $r_{ij}$ are rotation parameters and $T_x$, $T_y$ and $T_z$ are translations.

In one exemplary embodiment, a face region is detected from within a video frame of video footage using the Viola-Jones algorithm provided by the Computer Vision ToolBox MATLAB (Math Works, Natick, Va.), as well as the PittPatt SDK version 5.2.2 (acquired by Google). Robust facial features within the frame are identified using the Harris corner detection algorithm. The robust facial features are tracked between consecutive frames using the Kanade Lucas Tomasi (KLT) point tracker also available in MATLAB. In some embodiments a non reflective similarity transformation is generated from the variation in the tracked points between subsequent frames using a POSIT algorithm. The inverse similarity transformation is then applied as an offset to each frame to compensate for changes in the position of facial features between subsequent frames. The facial features are thereby computationally held in the initial position. The region around each eye is able to be cropped in each frame to isolate the eye movement from head movement.

Figure 13:
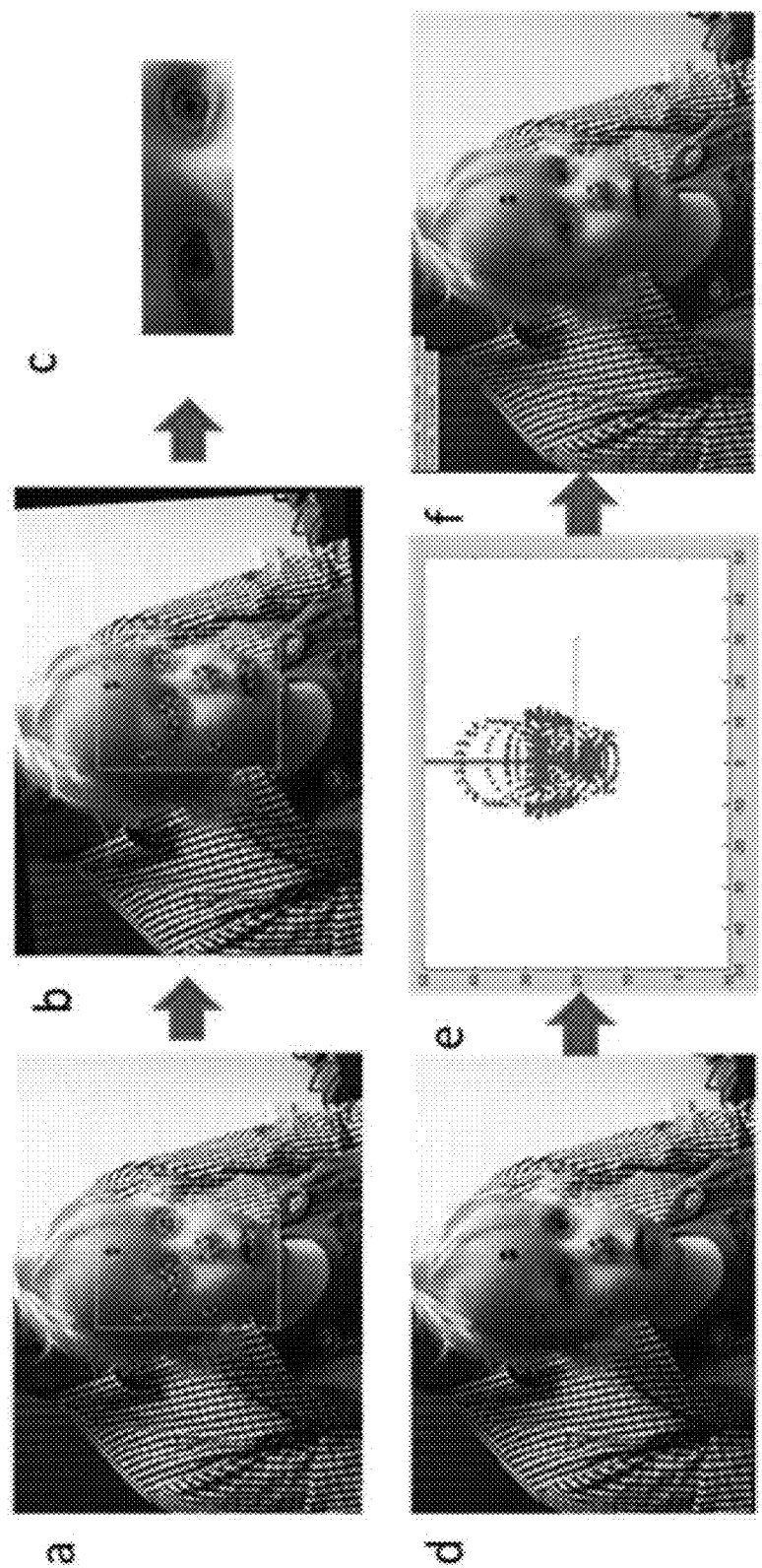
FIG. 13 shows the head 3D pose estimation and stabilization procedure.

FIG. 13 outlines a manual process to compare the accuracy of the automated exemplary process. FIG. 13(d) shows visual markers manually placed on a subjects' face prior to the video footage being recorded. The visual markers provide a clear point from which movement can be measured in the recorded footage. For each frame in the recorded footage, five corner points of each marker were selected manually using the MATLAB ginput command. The order in which the features were selected was consistent across frames to maintain correspondence of features from frame to frame. A Kalman filter was used to smooth the feature tracking because manual point selection introduces noise. Four references points were inserted into each recording and tracked across each video frames. Superimposing these points allowed differences between manual and automated stabilisation to be calculated. Coordinates of these points were compared between frames manually stabilised and frames automatically stabilised.

Figure 14:
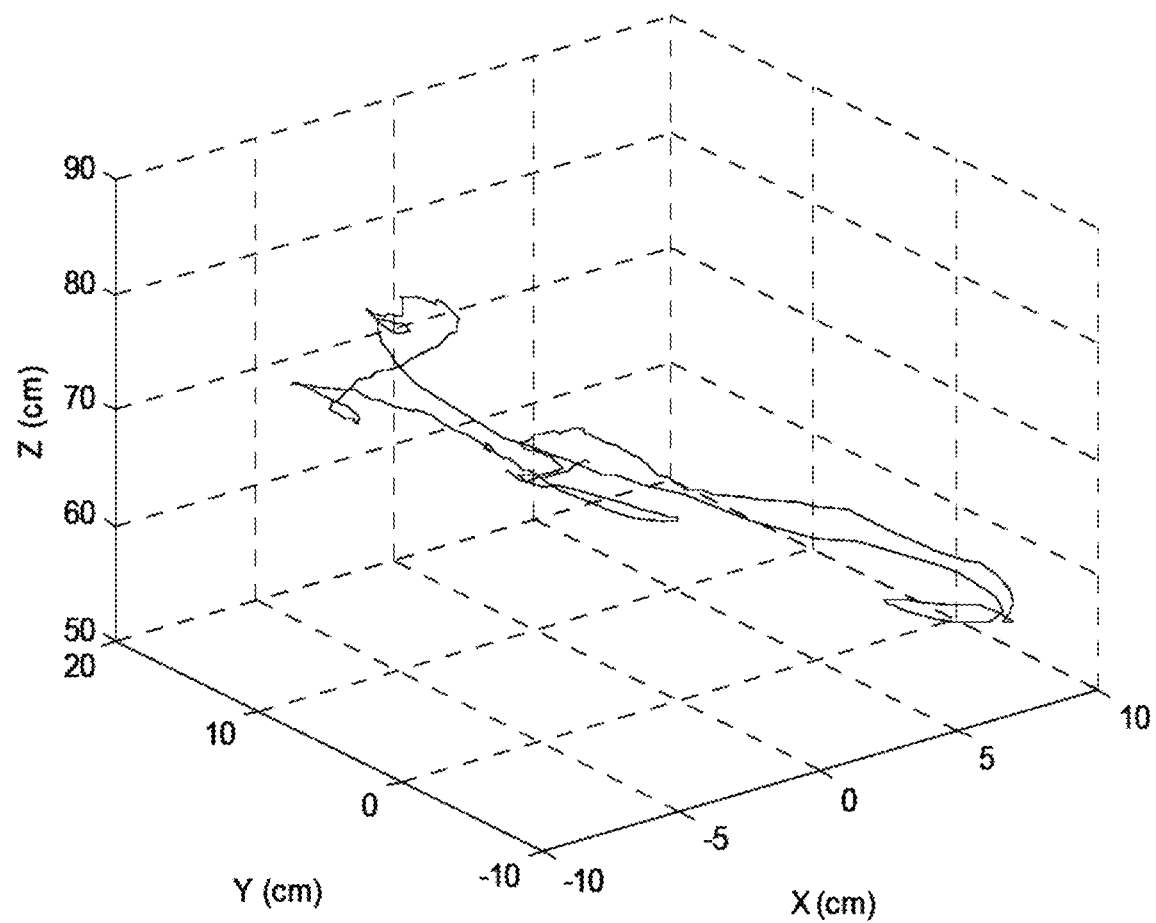
FIG. 14 shows the head trajectory estimation for a length of video footage in 3D space.

FIG. 13(a) shows Harris corners located in the automatically detected face region. FIG. 13(b) shows a stabilised video with the eye region "locked" to the centre of each frame. FIG. 13(c) shows the region around the eyes was cropped. FIG. 13(d) shows markers with manually selected centre points. FIG. 13(e) shows 3D pose estimation was determined by a POSIT algorithm where units are in centimetres. FIG. 13(f) shows re-projection of the manually selected marker points showing estimated head pose. FIG. 14 illustrates the head trajectory estimation for a length of video footage in 3D space.

Figure 12:
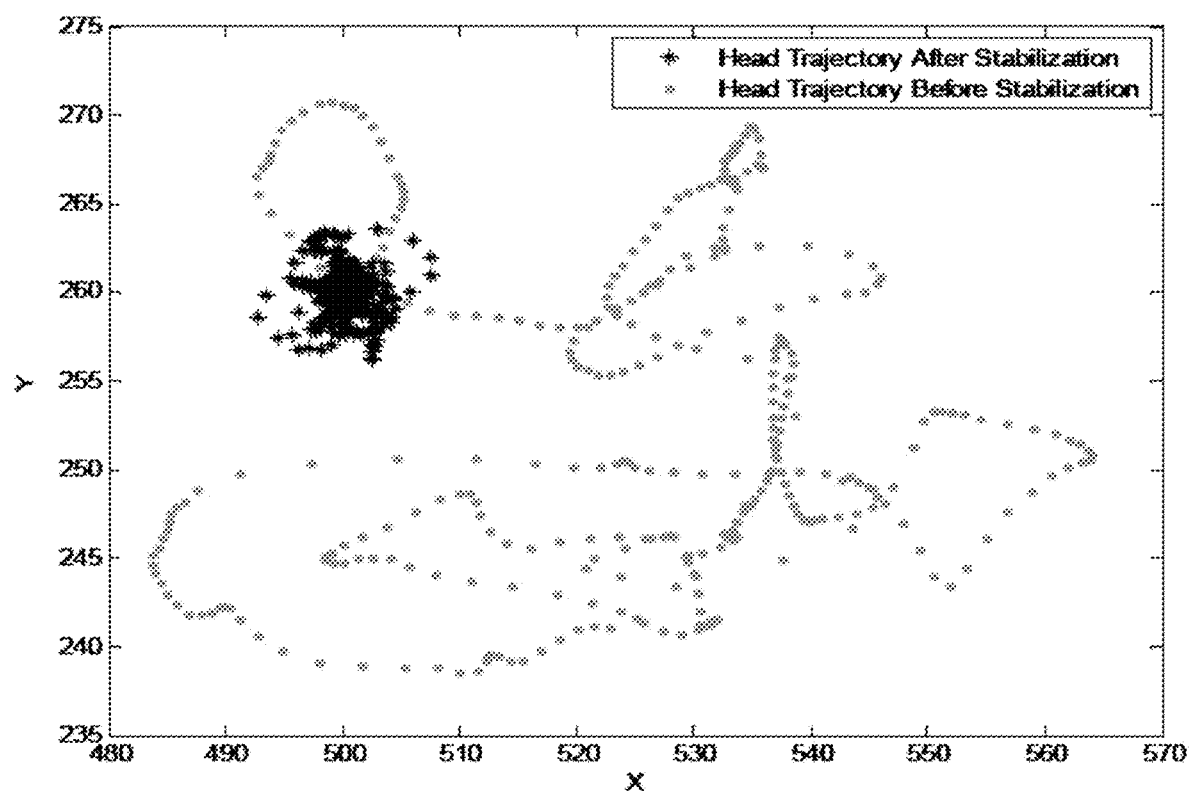
FIG. 12 shows raw and stabilised head trajectory according to another embodiment of the invention.

FIG. 12 has '+' symbols showing the trajectory of determined facial features within an example length of video footage. The '*' symbols show the effectively stabilised result after the inverse transformation map has been applied to each frame.

In FIG. 12, the faces are localised to a coordinate of (523.8037, 253.3558)±(18.6676, 8.9088) pixels prior to stabilisation, and (500.4114, 260.0309)±(1.8828, 1.4282) after stabilisation. The resulting stabilised footage exhibits a tight grouping of the facial feature locations which in turn illustrates substantial stabilisation of head portion compared to the original footage. The stabilised footage is then able to be consistently cropped to a desired region.

The average mean squared error between automatic and manual stabilization was 7.7494 pixels. Percentage error of 3D pose estimation was 0.2428%. This data indicates that a more labour intensive manual tracking approach involving markers, although robust, is no longer necessary to achieve stabilised video footage that is useful for many purposes, and in particular is useful for use with the above described OKN detection process.

In some embodiments the head trajectory information is used to improve the eye velocity information. In some embodiments the head trajectory information is offset against the eye tracking information to substantially remove eye velocity information caused by head movement. For example, data relating to the velocity of head movement can be offset against data relating to eye movement so error caused by non zero head velocity is substantially reduced or removed from the eye velocity information.

Where in the foregoing description reference has been made to elements or integers having known equivalents, then such equivalents are included as if they were individually set forth. Although the invention has been described by way of example and with reference to particular embodiments, it is to be understood that modifications and/or improvements may be made without departing from the scope of the invention as set out in the claims.

The invention claimed is:

1. A method of evaluating visual performance or visual health to detect vision problems comprising:
providing a visual stimulus in front of eye(s) of a subject, the stimulus effective to elicit optokinetic nystagmus,
obtaining video footage of the subject watching the stimulus,
detecting at least part of an eyeball in at least two frames of the video footage,
applying an optical flow algorithm to the at least two frames of the video footage to extract pixel velocity information relating to linear movement of at least part of the eyeball in response to the stimulus, said pixel velocity information including both magnitude and direction information,
determining a statistical measure comprising an average pixel velocity from the pixel velocity information,
extracting head image trajectory information from the video footage by detecting at least part of a facial region of a head of the subject in at least two frames of the video footage and determining a measure of movement of the at least part of a facial region between the at least two frames, and compensating for the head movement within the video footage,
evaluating visual performance or visual health of the subject from the statistical measure, including comparing the determined pixel velocity information to healthy pixel velocity information to make a determination of a presence and/or strength of OKN, to identify whether the stimulus gained the subject's attention indicating the subject was able to see the stimulus; and outputting an indicator of visual performance or visual health based on whether the subject was able to see the stimulus.

2. An eye tracking system for evaluating visual performance or visual health to detect vision problems comprising:
a visual stimulus arranged to be in front of eye(s) of a subject, the stimulus operable to elicit optokinetic nystagmus,
a camera arranged to capture footage of an eye or eyes of the subject watching the visual stimulus, and
a controller configured to receive the footage of the eye and perform steps of:
detecting at least part of an eyeball in at least two frames of the footage,
applying an optical flow algorithm to the footage to thereby determine pixel velocity information between at least two frames of the footage relating to linear movement of at least part of the eyeball, said pixel velocity information including both magnitude and direction information,
determining a statistical measure comprising an average pixel velocity from the pixel velocity information,
extracting head image trajectory information from the video footage by detecting at least part of a facial region of a head of the subject in at least two frames of the video footage and determining a measure of movement of the at least part of a facial region between the at least two frames, and compensating for the head movement within the video footage,
evaluating visual function performance or visual health of the subject from the statistical measure, including comparing the determined pixel velocity information to healthy pixel velocity information to make a determination of a presence and/or strength of OKN, to identify whether the stimulus gained the subject's attention indicating the subject was able to see the stimulus; and
outputting an indicator of visual performance or visual health based on whether the subject was able to see the stimulus.

3. The method as claimed in claim 1, further comprising one or more steps of (in any order):
determining the pixel velocity magnitude and direction of the at least part of the eyeball from the pixel velocity information,
determining any velocity maxima and minima from the pixel velocity information,
comparing any velocity maxima or minima to a lower velocity threshold and discarding any velocity maxima or minima below the lower velocity threshold,
comparing any velocity maxima or minima to an upper velocity threshold and discarding any velocity maxima or minima above the upper velocity threshold,
comparing a distance between adjacent velocity maxima or minima in at least two frames to a frame threshold and discarding any velocity maxima or minima below the frame threshold,
determining any sole velocity maxima or sole velocity minima in the pixel velocity information and discarding sole velocity maxima or sole velocity minima, and
averaging the velocity maxima or minima of the pixel velocity magnitudes, and/or normalizing the velocity maxima or minima of the pixel velocity magnitudes.

4. The method as claimed in claim 1, wherein the at least part of the eyeball is a region of contrast discontinuity of the eyeball.

5. The method as claimed in claim 1, wherein the at least part of the eyeball is a limbus portion of the eyeball.

6. The method as claimed in claim 1, wherein the optical flow algorithm is a Lucas-Kanade optical flow algorithm.

7. The method as claimed in claim 1, wherein the optical flow algorithm is applied to determine pixel velocity information between consecutive frames of a length of video footage corresponding to several reset events.

8. The eye tracking system as claimed in claim 2, wherein the controller is configured to (in any order):
determine the pixel velocity magnitude and direction of the at least part of the eyeball from the pixel velocity information,
determine any velocity maxima and minima from the pixel velocity information,
compare any velocity maxima or minima to a lower velocity threshold and discarding any velocity maxima or minima below the lower velocity threshold,
compare any velocity maxima or minima to an upper velocity threshold and discarding any velocity maxima or minima above the upper velocity threshold,
compare a distance between adjacent velocity maxima or minima in at least two frames to a frame threshold and discarding any velocity maxima or minima below the frame threshold,
determine any sole velocity maxima or sole velocity minima in the pixel velocity information and discarding sole velocity maxima or sole velocity minima,
average the velocity maxima or minima of the pixel velocity magnitudes, and/or
normalizing the velocity maxima or minima of the pixel velocity magnitudes.

9. The eye tracking system as claimed in claim 2, wherein the at least part of the eyeball is a region of contrast discontinuity of the eyeball.

10. The eye tracking system as claimed in claim 2, wherein the at least part of the eyeball is a limbus portion of the eyeball.

11. The eye tracking system as claimed in claim 2, wherein the optical flow algorithm is a Lucas-Kanade optical flow algorithm.

12. The eye tracking system as claimed in claim 2, wherein the controller is configured to extract head image trajectory information from the video footage by:
detecting at least part of a facial region of a head image in at least two frames of the video footage,
determining a measure of movement of the at least part of a facial region of the head between the at least two frames, and
determining a transformation map from the measure of movement.

13. The eye tracking system as claimed in claim 12 wherein the controller is configured to determine a measure of movement of the facial feature between the at least two frames using a Kanade Lucas Tomasi (KLT) optical flow algorithm as a point tracker.

14. The eye tracking system as claimed in claim 2, wherein the controller is configured to compensate for head movement within video footage.

15. The eye tracking system as claimed in claim 14 wherein the controller is configured to compensate for the head movement within video footage by detecting a facial feature in at least two frames of the video footage, determining a measure of movement of the facial feature caused by head movement between the at least two frames, and combining the information on the movement of the facial feature with the pixel velocity information relating to linear movement of the eyeball.

16. The eye tracking system as claimed in claim 14 wherein the controller is configured to compensate for the head movement within video footage by moving or cropping frames in the video footage such that a facial region within the frames is held constant between frames.

17. The method as claimed in claim 1, including compensating for head movement within video footage.

18. The method as claimed in claim 17 including compensating for head movement within video footage by detecting a facial feature in at least two frames of the video footage, determining a measure of movement of the facial feature caused by head movement between the at least two frames, and combining the information on the movement of the facial feature the pixel velocity information relating to linear movement of the eyeball.

19. The method as claimed in claim 17 including compensating for the head movement within video footage by moving or cropping frames in the video footage such that a facial region within the frames is held constant between frames.

20. A method of evaluating visual performance or visual health to detect vision problems, comprising:
   providing a visual stimulus in front of eye(s) of a subject, the stimulus effective to elicit optokinetic nystagmus,
   obtaining video footage of the subject watching the stimulus,
   detecting at least part of an eyeball of the subject and linear movement of the eyeball within the video footage by applying an optical flow algorithm to the video footage to extract pixel velocity information relating to linear movement of at least part of the eyeball in response to the stimulus, while also detecting movement of a head of the subject from movement of a facial feature other than an eyeball within the video footage, and compensating for the head movement within the video footage, to determine a presence of optokinetic nystagmus in response to the stimulus, and
   evaluating visual performance or visual health from the presence or absence or strength of optokinetic nystagmus, including comparing the determined pixel velocity information to healthy pixel velocity information to make a determination of a presence and/or strength of OKN, to identify whether the stimulus gained the subject's attention indicating the subject was able to see the stimulus; and
   outputting an indicator of visual performance or visual health based on whether the subject was able to see the stimulus.

* * * * *